(12) United States Patent
Rohde et al.

(10) Patent No.: US 8,155,270 B2
(45) Date of Patent: Apr. 10, 2012

(54) SYNERGISTIC ENERGY-DISPERSIVE AND WAVELENGTH-DISPERSIVE X-RAY SPECTROMETRY

(75) Inventors: David B. Rohde, Madison, WI (US); Patrick Paul Camus, Middleton, WI (US); Gregory S. Fritz, Verona, WI (US)

(73) Assignee: Thermo Electron Scientific Instruments LLC, Madison, WI (US)

( * ) Notice: Subject to any disclaimer, the term of this patent is extended or adjusted under 35 U.S.C. 154(b) by 194 days.

(21) Appl. No.: 12/512,876

(22) Filed: Jul. 30, 2009

(65) Prior Publication Data

US 2010/0027748 A1  Feb. 4, 2010

Related U.S. Application Data

(60) Provisional application No. 61/085,969, filed on Aug. 4, 2008.

(51) Int. Cl.
  *G01T 1/36* (2006.01)
  *G01N 23/201* (2006.01)
  *G01N 23/22* (2006.01)

(52) U.S. Cl. ............... 378/83; 378/82; 378/87; 378/90

(58) Field of Classification Search .......... 378/70, 378/82–86, 88, 90, 95, 210
  See application file for complete search history.

(56) References Cited

U.S. PATENT DOCUMENTS

| | | | |
|---|---|---|---|
| 4,988,872 A * | 1/1991 | Nagatsuka et al. | 850/9 |
| 5,912,940 A * | 6/1999 | O'Hara | 378/82 |
| 5,926,522 A | 7/1999 | McCarthy et al. | |
| 6,292,532 B1 * | 9/2001 | Kawahara et al. | 378/49 |
| 2003/0169846 A1 * | 9/2003 | Janik et al. | 378/90 |
| 2008/0067379 A1 * | 3/2008 | Notoya | 250/310 |
| 2008/0111072 A1 * | 5/2008 | Takakura | 250/310 |

FOREIGN PATENT DOCUMENTS

JP   2007-285786 A   11/2007

OTHER PUBLICATIONS

White Paper, "How WDS and Parallel Beam Spectroscopy Work," Thermo Electron Scientific Instruments LLC (2007), p. 1-11.

* cited by examiner

*Primary Examiner* — Anastasia Midkiff
(74) *Attorney, Agent, or Firm* — DeWitt Ross & Stevens; Michael C. Staggs

(57) ABSTRACT

An X-ray spectroscope collects an energy-dispersive spectrum from a sample under analysis, and generates a list of candidate elements that may be present in the sample. A wavelength dispersive spectral collector is then tuned to obtain X-ray intensity measurements at the energies/wavelengths of some or all of the candidate elements, thereby verifying whether or not these candidate elements are in fact present in the sample. Additionally, the alignment of the wavelength dispersive spectral collector versus the sample can be optimized by tuning the wavelength dispersive spectral collector to the energy/wavelength of a selected one of the candidate elements—preferably one whose presence in the sample has been verified, or one which has a high likelihood of being present in the sample—and then varying the alignment of the wavelength dispersive spectral collector versus the sample until the wavelength dispersive spectral collector returns the maximum intensity reading for the selected candidate element. Intensity readings for the other candidate elements can then be collected at this optimized alignment.

17 Claims, 1 Drawing Sheet

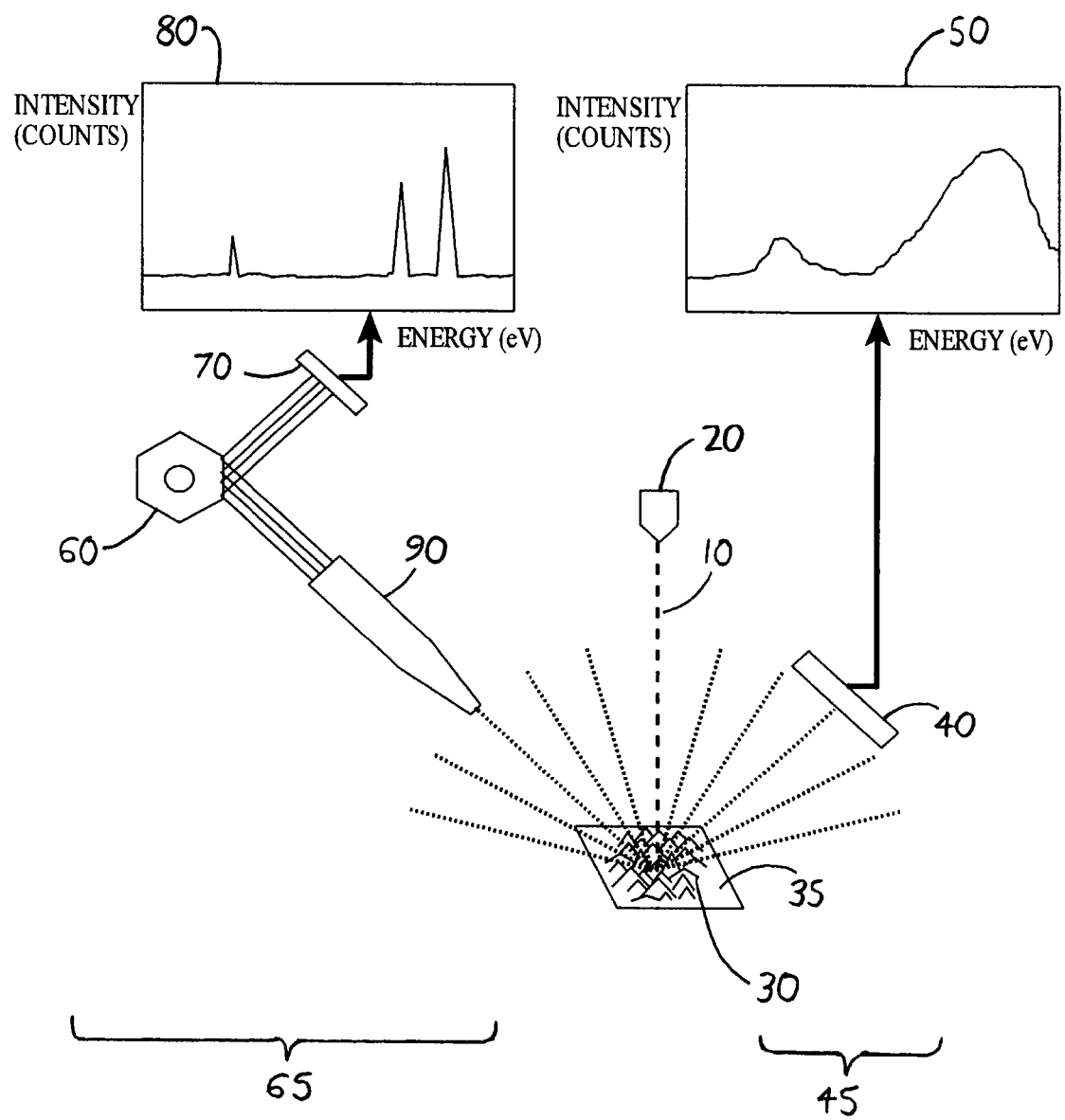

SYNERGISTIC ENERGY-DISPERSIVE AND WAVELENGTH-DISPERSIVE X-RAY SPECTROMETRY

CROSS-REFERENCE TO RELATED APPLICATIONS

This application claims priority under 35 USC §119(e) to U.S. Provisional Patent Application 61/085,969 filed 4 Aug. 2008, the entirety of which is incorporated by reference herein.

FIELD OF THE INVENTION

The invention relates generally to the field of X-ray spectroscopy, and more particularly to the fields of energy-dispersive X-ray spectroscopy and wavelength-dispersive X-ray spectroscopy.

BACKGROUND OF THE INVENTION

X-ray detectors are used in electron microscopes (such as scanning electron microscopes (SEMs), transmission electron microscopes (TEMs), and the like), X-ray spectrometers (such as X-ray fluorescence (XRF) spectrometers, particle-induced x-ray emission (PIXE) spectrometers, and the like), and other instruments to analyze the composition of materials. This is schematically illustrated in the accompanying FIG. 1, wherein an energy beam 10 such as an electron beam, proton beam, X-ray beam, gamma ray beam, or the like is directed from an emitter 20 toward a target location on a sample 30 to be analyzed. The emitter 20 can take the form of any appropriate beam emitter (e.g., a cathode in the case of an electron energy beam), and may be associated with beam focusing/steering devices (e.g., magnetic lenses for diverting an electron energy beam as desired), which are not shown in FIG. 1. The atoms of the sample 30 ionize in response to the incident energy beam 10, with electrons within the atoms transitioning between different orbital levels about their nuclei. (Such orbitals are often referred to as the K, L, M, and N shells, and the transitions between shells are often referred to as alpha transitions when they occur between two adjacent shells and beta transitions when they occur between two shells spaced by an intermediate shell.) These electron transitions release energy in the form of X-ray (X-ray photon) emissions from the sample 30, wherein the X-rays have energies and wavelengths which are characteristic of the atoms of the sample 30 from which they were emitted, i.e., they are characteristic of the elemental composition of the sample. Thus, the foregoing instruments can measure and analyze the X-ray energies and/or wavelengths to identify and quantify the elemental composition of the sample 30.

Such instruments also often scan the energy beam 10 across a series of target locations on the sample 30 (and/or the sample 30 is scanned beneath the beam 10) to build a "map" of the sample's composition over its area. Additionally, byproducts from the energy beam 10 can be captured at each target location and can be used to generate an image of the sample 30. For example, where the energy beam 10 is an electron beam, the image may depict the target location's backscattered electrons (electrons from the energy beam 10 which were "reflected" from the target location), or the target location's secondary electrons (electrons knocked out of the specimen by the energy beam 10). In either case, the image provides a visual representation of the target location, though the visual representation may not correspond to the target location's appearance if viewed by the eye under standard light. For example, a backscattered electron image effectively provides a view of the target location's density, and a secondary electron image effectively provides a view of the target location's surface roughness. The generated image(s) can be displayed along with the aforementioned elemental composition data for various regions of the sample 30 depicted in the image(s), providing a user valuable understanding of the nature of the sample 30.

The accuracy of the elemental composition data, and the speed and ease of its collection, depends heavily on how it is generated. In energy dispersive spectrometry (EDS), an EDS detector 40—e.g., a Silicon Drift Detector (SDD), lithium-doped silicon (SiLi) detector, microcalorimeter, photodiode, silicon multi-cathode detector (SMCD), PiN diode, or similar device—detects the X-ray photons emitted from the target location on the sample 30 and their energies (usually measured as voltages), and the relative numbers (counts) of the detected photons and their energies serve as the basis for elemental analysis. The photon counts and energies form a spectrum—more specifically, an energy dispersive spectrum—which is often presented as a histogram wherein the counts from the sample are plotted versus their energy (with an exemplary spectrum of this nature being depicted at 50). The number of counts at specific energies or energy ranges then serve to indicate the aforementioned electron transitions, which can serve as characteristic "fingerprints" of particular elements. Stated differently, a high count or "peak" at a particular energy or energy range can serve to indicate the presence of a particular element within the sample. Thus, by compiling a spectrum containing the counts and energies of the emitted photons and comparing it to reference spectra (spectra generated from substances having known elemental composition), or otherwise identifying the elements giving rise to the peaks, one may obtain information regarding the elements present in the specimen. Additionally, the relative heights of the peaks—i.e., their counts or photon intensities—can provide an indication of the relative quantities of the elements present.

One problem with EDS is that it has somewhat poor resolution, in that the peaks of certain different elements overlap (i.e., certain elements generate peaks which rest at the same energies or energy ranges). As an example, sulfur K-alpha peaks, molybdenum L-alpha peaks, and lead M-alpha peaks display across the same energies or energy ranges. Overlapping peaks can sometimes be "deconvolved" into individual peaks by, for example, comparing a measured EDS spectrum to reference spectra, and determining the reference spectra that most likely combine to result in the measured spectrum. However, because deconvolution can sometimes result in incorrect determination of the elements present and their relative amounts, followup analysis is sometimes needed to determine whether its results are correct.

An alternative to EDS is wavelength dispersive spectroscopy (WDS), which uses Bragg's law of diffraction to "sort" the X-ray photons into their separate wavelengths, and the counts and energies of the photons at the various wavelengths then serve to identify the elements within the sample 30. WDS is also schematically illustrated at the left-hand side of FIG. 1, wherein photons emitted from the target location on the sample 30 are directed at a diffractor 60. Depending on the characteristics of the diffractor 60 and its orientation with respect to the incident photons, photons having a certain wavelength will reflect constructively and can be strongly measured at a WDS detector 70, while photons at other wavelengths will destructively interfere and weakly register at the detector 70. Thus, by changing the angle of the diffractor 60 with respect to the sample 30 (and the angle and/or position of the detector 70 as well, since the angle between the diffractor 60 with respect to the incident photons must generally be equal to the angle between the diffractor 60 and detector 70), and/or by changing the diffractor 60 itself (as by rotating the hexagonal diffractor 60 to expose different faces—which are formed of different crystal diffractors—to the incident X-rays), one may scan through all relevant wavelengths to again generate a spectrum of photon counts/intensities and energies which serves to characterize the elemental composition of the sample 30. The elemental peaks in WDS spectra tend to have significantly higher resolution (i.e., the peaks appear across narrower energy ranges and are "sharper"), with an exemplary WDS spectrum being illustrated in FIG. 1 at 80. This helps to avoid the problem of peak overlap that occurs with EDS. (It is notable that EDS and WDS systems are not conventionally combined in the same device as shown in FIG. 1, and they are shown in combined form here merely for ease of discussion, and also for sake of the discussion of the invention below.) However, WDS has the disadvantage that it is time-consuming: it takes time to tune the WDS spectral collector (i.e., to position the diffractor 60 and detector 70) to scan across a range of wavelengths, and to collect measurements at each resulting wavelength setting. As a result, it is common to tune the WDS spectral collector to collect measurements only at the wavelengths of the emission lines (i.e., peaks) of elements of interest, usually elements whose presence is suspected in the sample 30. This approach can therefore fail to detect certain elements if relevant wavelengths are skipped. WDS also bears difficulties in that it is extremely sensitive to the alignment between the sample 30, diffractor 60, and detector 70: the detector 70 and the target location on the sample 30 must both be located at the same angle with respect to the diffractor 60, and the detector 70 only properly registers photons traveling along the path defined by this relationship. As a result, if the target location on the sample 30 is not located at the same angle with respect to the diffractor 60 as the detector 70, the detector 70 will receive few or no photons, resulting in no or low detector 70 readings. Difficulties in attaining proper alignment can be compounded by drift in the energy beam 10—its axis can change over time—and by the topology of the sample 30 (e.g., differences in surface height, as shown in FIG. 1), factors which lead to variability in the target location on the sample 30. As discussed in U.S. Pat. No. 5,926,522, which usefully contains more details on WDS and EDS (and which is incorporated by reference herein), a collection optic 90 (such as a polycapillary lens/optic) can usefully be situated between the sample 30 and diffractor 60 to capture photons traveling along the aforementioned path, as well as photons traveling along slightly divergent paths, and focus and collimate them so that they travel along the desired path for detection at the detector 70. In effect, the collection optic 90 increases the field of view of the detector 70, thus increasing the number of received photons and allowing reduction in photon collection times. Nevertheless, the system is still sensitive to misalignment.

Owing to the aforementioned difficulties, further increases in accuracy, speed, and ease of WDS (and EDS) would naturally be welcomed.

BRIEF DESCRIPTION OF THE DRAWINGS

FIG. 1 is a simplified schematic view of an exemplary X-ray spectroscopy arrangement wherein an energy beam 10 is directed at a target location on the sample 30, with resulting X-ray emissions from the sample 30 being detected by an EDS spectral collector (represented by an EDS detector 40) and also by a WDS spectral collector (represented by a collection optic 90, a diffractor 60, and a detector 70), with a resulting EDS spectrum being depicted at 50 and a resulting WDS spectrum being depicted at 80.

DETAILED DESCRIPTION OF PREFERRED VERSIONS OF THE INVENTION

The invention, which is defined by the claims set forth at the end of this document, is directed to systems which use both EDS and WDS to at least partially alleviate the aforementioned problems. A basic understanding of some of the features of preferred versions of the invention can be attained from a review of the following discussion, which makes reference to the accompanying drawing of an exemplary arrangement for the invention.

The invention may utilize an arrangement exemplified by the one in FIG. 1, wherein an X-ray spectrometer includes a sample mount 35; an energy beam emitter 20 arranged to emit an energy beam 10 toward a sample 30 on the sample mount 35; and an energy dispersive spectral collector 45 and a wavelength dispersive spectral collector 65. The energy dispersive spectral collector 45 is arranged to receive X-rays emitted from the sample 30, wherein the energy dispersive spectral collector 45 has an energy dispersive spectrum (EDS) detector 40. The wavelength dispersive spectral collector 65 is similarly arranged to receive X-rays emitted from the sample 30, and includes at least a diffractor 60 receiving X-rays emitted from the sample 30, and a wavelength dispersive spectrum (WDS) detector 70 receiving X-rays from the diffractor 60 (and also preferably a collection optic 90 receiving X-rays emitted from the sample 30 and providing such X-rays to the diffractor 60).

The energy dispersive spectral collector 45 can be used to obtain an energy dispersive spectrum 50 from a target location on the sample 30, and one or more candidate elements—i.e., elements that may be present at the target location on the sample 30—can be identified from the energy dispersive spectrum 50 in conventional fashion, e.g., by comparison of the EDS spectrum 50 to reference spectra, by application of deconvolution schemes, etc. The candidate elements can be output to a user if desired, and can also be used in at least one of the following ways.

Initially, they can be used to optimize the position of the wavelength dispersive spectral collector 65 with respect to the target location on the sample 30, such that the wavelength dispersive spectral collector 65 is better aligned to obtain high-quality intensity measurements—e.g., to collect the maximum amount of emitted photons—from the target location. The wavelength dispersive spectral collector 65 can be tuned to obtain an intensity reading for a selected one of the identified candidate elements by adjusting its diffractor 60, detector 70, and/or other components to the proper wavelength/energy setting to obtain an intensity reading for the selected candidate element from the target location on the sample 30. After obtaining this initial intensity reading, the wavelength dispersive spectral collector 65 can then be repositioned (realigned) with respect to the target location on the sample 30 by moving it in one or more degrees of freedom, preferably by simply translating the wavelength dispersive spectral collector 65 (and/or the sample 30) along one or more axes. When the wavelength dispersive spectral collector 65 then obtains another intensity reading for the candidate element from the target location on the sample 30, the new intensity reading is taken from a different alignment than the prior intensity reading. This process of collecting intensity readings for the candidate element at different alignments with respect to the target location on the sample 30 can then be repeated several times, if desired. The collected intensity readings can then be compared to identify the position(s) of the wavelength dispersive spectral collector 65 and/or the sample 30 at which the maximum intensity reading was obtained. This likely represents the position(s) of the wavelength dispersive spectral collector 65 and/or the sample 30 at which the wavelength dispersive spectral collector 65 is best aligned with respect to the target location on the sample 30. Since the position of the wavelength dispersive spectral collector 65 is varied with respect to the target location on the sample 30 to maximize the reading intensity for the selected candidate element—an element which also manifested itself (or at least seemed to do so) in the collected EDS spectrum 50—the position which generates the highest intensity reading is likely to correspond (or at least more closely correspond) to an aligned state between the target location on the sample 30, the diffractor 60, and the WDS detector 70 (as well as any collection optic 90 situated between the sample 30 and the diffractor 60).

Once the position generating the maximum intensity reading is identified, the wavelength dispersive spectral collector 65 and/or the sample 30 can be moved back to this position (if they are not already at this position), and the wavelength dispersive spectral collector 65 can be tuned to collect intensity readings from the target location on the sample 30 for other candidate elements. The collected intensity readings for the various candidate elements may be compiled to build the WDS spectrum 80. Collection time can be optimized by taking intensity readings only at wavelengths/energies where the EDS spectrum 50 has indicated that a candidate element is possibly present. Most preferably, this is done by starting collection at the wavelengths/energies of the candidate elements which are deemed most likely to be present during analysis of the EDS spectrum 50. Data quality—i.e., the number of detected counts, and thus spectral resolution—is enhanced by "hunting" for the collector 65/sample 30 alignment which generates the highest intensity reading for a candidate element, and then taking WDS intensity readings once alignment has been optimized.

On the other hand, if changing the position between the wavelength dispersive spectral collector 65 and the target location does not result in meaningful changes in intensity readings, and/or if the intensity readings have little or no difference from "background" intensity readings (as discussed below), this may indicate that the selected candidate element is not in fact present at the target location on the sample 30—for example, perhaps the presence of the candidate element was incorrectly derived from the EDS spectrum 50 owing to a deconvolution error. When this occurs, the candidate element can be deleted from the list of candidate elements identified from the EDS spectrum 50. In this manner, the WDS intensity readings are used to verify candidate elements identified from measured EDS spectra, and to eliminate candidate elements which are not in fact present. This verification can be performed even if the aforementioned alignment optimization procedure is not performed. For example, for each of the candidate elements returned from analysis of an EDS spectrum 50 (or for at least some of these candidate elements), the wavelength dispersive spectral collector 65 can be tuned to obtain an intensity reading for the candidate element, and intensity readings can be collected at each setting from the target location on the sample 30. The intensity readings can be analyzed to determine whether they indicate the presence of their candidate elements by, for example, comparing them to one or more "background" intensity readings: intensity readings obtained at wavelengths/energies at which no elements generate characteristic intensity readings, with these intensity readings thereby representing background noise. (Preferably, intensity readings are obtained at several such wavelengths/energies and are then averaged, summed, or otherwise combined to obtain an "average" background intensity reading which is representative of background noise.) If an intensity reading for a candidate element is similar to an intensity reading characteristic of background noise, then the candidate element is probably not present at the target location on the sample 30, and the candidate element should then be eliminated from the list of candidate elements. On the other hand, if there is a significant difference between the background intensity reading and the intensity reading for the candidate element, this can indicate that the candidate element is likely present at the target location.

When performing the aforementioned alignment optimization procedure, once one or more candidate elements are identified from the EDS spectrum 50, it is preferable to select the candidate element for use in alignment—i.e., to select the candidate element to which the wavelength dispersive spectral collector 65 will be tuned, and whose maximum intensity signal will be "hunted" at the target location—on the basis of one or more of the following factors. (Preferably, all of the following factors are considered, with their weight/importance being listed in decreasing order.)

First, the selected candidate element should naturally be one for which the wavelength dispersive spectral collector 65 can obtain an intensity reading. In some cases, it is possible that the EDS spectrum 50 may indicate the presence of an element which is not measurable (or not efficiently measurable) by the wavelength dispersive spectral collector 65, for example, because the diffractor 60 cannot accommodate tuning of the wavelength dispersive spectral collector 65 to the wavelength/energy at which the element is accurately measured. Often, wavelength dispersive spectral collectors 65 are constructed to optimally detect one or more specific elements (e.g., Si, Fe, Al): the intensities of these elements are measured more easily and accurately than for other elements, usually owing to careful selection of the diffractor 60. It is preferred that the selected candidate element is such an element, one for which the wavelength dispersive spectral collector 65 can most efficiently obtain an intensity reading.

Second, the selected candidate element is preferably one which has one of the highest peaks (counts or intensities) within the energy dispersive spectrum 50. Such a candidate element should then have an intensity which is readily measurable by the wavelength dispersive spectral collector 65, provided the candidate element is truly present in the sample 30. A particularly preferred method for selecting the candidate element for use in alignment optimization is to choose a candidate element which has a peak height within the energy dispersive spectrum 50 which is greater than or equal to approximately 5-15% of the sum of all of the peak heights within the energy dispersive spectrum 50. By choosing, for example, a candidate element having an EDS spectrum peak which has counts of at least 10% of the total counts for all of the peaks in the EDS spectrum 50, the selection of a "trivial" candidate element—one which might register only a weak WDS intensity, and which might lead to less optimal WDS alignment—is better avoided.

Third, the selected candidate element is preferably one which has high likelihood of being accurately identified from the EDS spectrum 50. For example, the identity of a candidate element may be uncertain because its peak is at an energy shared by numerous elements (with all of these elements thereby possibly being candidate elements). It may be preferable to avoid use of such candidate elements in alignment efforts unless the likelihood of a candidate's presence within the sample 30 can be assessed with a reasonable degree of certainty (e.g., by deconvolution or other methods). Thus, when cross-referencing a peak within the energy dispersive spectrum 50 versus a number of candidate elements to generate the list of most likely candidate elements for the peak, it is preferable to select the candidate element for use in alignment efforts as being the candidate element which most likely represents the peak.

Once alignment between the wavelength dispersive spectral collector 65 and the sample 30 is optimized, and once intensity readings for one or more of the candidate elements have been collected, the intensity readings can be used in quantitative analysis to determine measures of the amounts of each element present in the sample 30. For example, the measured intensity reading for an element can be compared to a standard/reference intensity reading for the element (as by calculating the ratio of the measured reading to the standard reading), whereby the comparison is indicative of the quantitative amount of the selected candidate element at the target location on the sample 30. Such quantitative analysis can also or alternatively be performed using peaks/intensities from the EDS spectrum 50, but WDS readings are preferably used because the higher resolution of WDS intensity readings can yield more meaningful results.

Preferably, the aforementioned EDS spectrum 50 and the WDS spectrum 80 are visually presented to the user on a computer monitor or other display, perhaps in conjunction with an image of the target location on the sample 30 from which the spectra were obtained. These can be presented along with the name(s) of the elements represented by each peak, with these elements being confirmed by comparison of WDS intensity readings to background readings, as mentioned above. These element names might be visually overlaid on the displayed peaks along with the results of any quantitative analysis performed on the elements (e.g., along with the absolute or relative amounts of each element). Most preferably, the sample 30 and/or the energy dispersive spectral collector 45 and wavelength dispersive spectral collector 65 are indexed so that a series of spectra and other readings are obtained from a series of target locations situated about the sample 30, whereby a map of the sample's elemental composition can be constructed.

It should be apparent from the foregoing discussion that the various steps/functions of the invention (identifying candidate elements from EDS results, optimizing the position of the wavelength dispersive spectral collector by use of such candidate elements, verifying the presence of EDS-identified candidate elements by use of WDS, etc.) can be performed in automated or semi-automated form by appropriate software and/or hardware elements provided in conjunction with spectrometer components such as those shown in FIG. 1. Such software and/or hardware elements are only conceptually illustrated in FIG. 1, e.g., via the EDS and WDS spectra 50 and 80, which are typically shown on a computer monitor or similar display. Most preferably, any software and/or hardware components implementing the invention are simply provided as additions and/or modifications to conventional preexisting EDS and/or WDS hardware/software; for example, preexisting EDS hardware/software can be adapted to form the invention (as by combining it with preexisting WDS hardware/software and making appropriate modifications), or conversely preexisting WDS hardware/software can be adapted to form the invention.

It should be understood that the versions of the invention described above are merely exemplary, and the invention is not intended to be limited to these versions. Rather, the scope of rights to the invention is limited only by the claims set out below, and the invention encompasses all different versions that fall literally or equivalently within the scope of these claims.

What is claimed is:

1. A method for obtaining X-ray spectra in an X-ray spectrometer including:
    an energy beam emitter arranged to emit an energy beam toward a sample on a sample mount;
    an energy dispersive spectral collector arranged to receive X-rays emitted from the sample, the energy dispersive spectral collector having an energy dispersive spectrum (EDS) detector;
    a wavelength dispersive spectral collector arranged to receive X-rays emitted from the sample, the wavelength dispersive spectral collector having a wavelength dispersive spectrum (WDS) detector and a diffractor, with the diffractor providing X-rays from the sample to the wavelength dispersive spectrum (WDS) detector;
    the method including the steps of:
    directing an energy beam at a target location on the sample;
    obtaining an energy dispersive spectrum from the target location via the energy dispersive spectral collector;
    identifying from the energy dispersive spectrum a list of one or more candidate elements, each listed candidate element representing an element that may be present at the target location on the sample;
    obtaining one or more WDS intensity readings at the target location via the wavelength dispersive spectrum (WDS) detector, and
    performing at least one of the steps of:
        optimizing the position of the wavelength dispersive spectral collector with respect to the target location on the sample, wherein at least one of the wavelength dispersive spectral collector and the target location is repositioned with respect to the other such that a maximum WDS intensity reading is obtained for one of the listed candidate elements, and
        verifying the presence of at least one of the candidate elements in the list, wherein the candidate element is deleted from the list if the WDS intensity reading for the candidate element is at least substantially similar to a WDS intensity reading characteristic of background noise.

2. The method of claim 1 wherein the step of optimizing the position of the wavelength dispersive spectral collector with respect to the target location on the sample includes:
    tuning the wavelength dispersive spectral collector to obtain a WDS intensity reading for a selected one of the identified candidate elements;
    obtaining a WDS intensity reading for the selected candidate element from the target location on the sample;
    performing the following substeps at least once:
        situating at least a portion of the wavelength dispersive spectral collector at a new position with respect to the target location on the sample;
        obtaining another WDS intensity reading for the selected candidate element from the target location on the sample;
    identifying the position at which the maximum WDS intensity reading was obtained.

3. The method of claim 2 wherein the selected candidate element is one of the candidate elements for which the wavelength dispersive spectral collector can most efficiently obtain a WDS intensity reading.

4. The method of claim 2 wherein the selected candidate element is one of the candidate elements having one of the highest peaks within the energy dispersive spectrum.

5. The method of claim 4 wherein:
the selected candidate element has a peak height within the energy dispersive spectrum which is greater than or equal to a threshold percentage of the sum of all of the peak heights within the energy dispersive spectrum; and
the threshold percentage is between approximately 5-15%.

6. The method of claim 2:
wherein the step of identifying one or more candidate elements from the energy dispersive spectrum includes:
cross-referencing peaks within the energy dispersive spectrum versus a number of candidate elements, and determining, for each peak, the one or more most likely candidate elements that the peak represents; and
wherein the selected candidate element is a candidate element having one of the greatest likelihoods of accurately representing one of the peaks.

7. The method of claim 2:
wherein at least two candidate elements are identified from the energy dispersive spectrum; and
further comprising the step of obtaining a WDS intensity reading for a second selected candidate element from the target location on the sample, with the wavelength dispersive spectral collector being situated at the position at which the maximum WDS intensity reading was obtained.

8. The method of claim 2 further comprising the step of obtaining WDS intensity readings for all of the identified candidate elements from the target location on the sample, with the wavelength dispersive spectral collector being situated at the position at which the maximum WDS intensity reading was obtained.

9. The method of claim 2 further comprising the steps of:
at the position at which the maximum WDS intensity reading was obtained, tuning the wavelength dispersive spectral collector to obtain a WDS intensity reading at a wavelength at which no elements generate a characteristic WDS intensity reading, thereby obtaining a WDS intensity reading characteristic of background noise;
comparing the maximum WDS intensity reading with the WDS intensity reading characteristic of background noise,
whereby a significant difference between the maximum WDS intensity reading and the WDS intensity reading characteristic of background noise is indicative of the presence of the selected candidate element at the target location on the sample.

10. The method of claim 9 further comprising the steps of:
at the position at which the maximum WDS intensity reading was obtained, tuning the wavelength dispersive spectral collector to obtain a WDS intensity reading at a second wavelength at which no elements generate a characteristic WDS intensity reading, thereby obtaining an second WDS intensity reading characteristic of background noise;
combining the WDS intensity readings characteristic of background noise into a single WDS intensity reading characteristic of background noise.

11. The method of claim 9 further including the following steps for each of the identified candidate elements:
tuning the wavelength dispersive spectral collector to obtain a WDS intensity reading for the candidate element;
obtaining a WDS intensity reading for the selected candidate element from the target location on the sample;
tuning the wavelength dispersive spectral collector to obtain a WDS intensity reading at a wavelength at which no elements generate a characteristic WDS intensity reading, thereby obtaining a WDS intensity reading characteristic of background noise;
comparing the WDS intensity reading for the candidate element with the WDS intensity reading characteristic of background noise,
whereby a significant difference between the WDS intensity reading for the candidate element and the WDS intensity reading characteristic of background noise is indicative of the presence of the candidate element at the target location on the sample.

12. The method of claim 2 further comprising the step of comparing the maximum WDS intensity reading to a standard WDS intensity reading for the selected candidate element, whereby the comparison is indicative of the quantitative amount of the selected candidate element at the target location on the sample.

13. The method of claim 1 wherein the step of verifying the presence of at least one of the candidate elements in the list includes the steps of:
tuning the wavelength dispersive spectral collector to obtain a WDS intensity reading for the candidate element;
obtaining a WDS intensity reading for the candidate element from the target location on the sample;
tuning the wavelength dispersive spectral collector to obtain a WDS intensity reading at a wavelength at which no elements generate a characteristic WDS intensity reading, thereby obtaining a WDS intensity reading characteristic of background noise;
comparing the WDS intensity reading for the candidate element with the WDS intensity reading characteristic of background noise,
whereby a significant difference between the WDS intensity reading for the candidate element and the WDS intensity reading characteristic of background noise is indicative of the presence of the candidate element at the target location on the sample.

14. The method of claim 13 further comprising the steps of:
tuning the wavelength dispersive spectral collector to obtain a WDS intensity reading at a second wavelength at which no elements generate a characteristic WDS intensity reading, thereby obtaining a second WDS intensity reading characteristic of background noise;
combining the WDS intensity readings characteristic of background noise into a single WDS intensity reading characteristic of background noise.

15. The method of claim 13 wherein if a comparison of the WDS intensity reading for the candidate element with the WDS intensity reading characteristic of background noise indicates that the presence of its candidate element is negligible at the target location on the sample, the candidate element is removed from the list.

16. The method of claim 13 further including the steps of:
confirming from each comparison of the WDS intensity reading for the candidate element with the WDS intensity reading characteristic of background noise whether the candidate element is present at the target location on the sample;
displaying in conjunction:
the energy dispersive spectrum obtained at the target location on the sample, and
the identity of each candidate element whose presence at the target location on the sample has been confirmed.

17. The method of claim 13 including the following steps after the WDS intensity reading for the candidate element is obtained from the target location on the sample:
    situating at least a portion of the wavelength dispersive spectral collector at a new position with respect to the target location on the sample;
    obtaining another WDS intensity reading for the candidate element from the target location on the sample; and
    identifying the position at which the maximum WDS intensity reading was obtained.

* * * * *